United States Patent [19]

Fujimiya et al.

[11] Patent Number: 5,069,769
[45] Date of Patent: Dec. 3, 1991

[54] ELECTROPHORESIS PATTERN READING SYSTEM OF FLUORESCENCE TYPE

[75] Inventors: Hitoshi Fujimiya; Shigeo Nakajima; Hisanori Nasu, all of Yokohama, Japan

[73] Assignee: Hitachi Software Engineering Co., Ltd., Yokohama, Japan

[21] Appl. No.: 533,853

[22] Filed: Jun. 6, 1990

[30] Foreign Application Priority Data

Jun. 7, 1989 [JP] Japan .................................. 1-145859

[51] Int. Cl.$^5$ ........................... C25B 1/00; C25B 7/00; B01D 61/42; C25D 13/00
[52] U.S. Cl. ............................... 204/182.8; 204/299 R
[58] Field of Search ............... 204/182.7, 182.8, 182.9, 204/299 R

[56] References Cited

U.S. PATENT DOCUMENTS

| 3,994,593 | 11/1976 | Kato et al. | 356/203 |
|---|---|---|---|
| 4,130,824 | 12/1978 | Amos et al. | 346/33 A |
| 4,675,095 | 6/1987 | Kambara et al. | 204/299 R |
| 4,720,788 | 1/1988 | Golias | 364/416 |
| 4,810,348 | 3/1989 | Sarrine et al. | 204/182.8 |

FOREIGN PATENT DOCUMENTS

| 0050386 | 4/1982 | European Pat. Off. |
| 0241904 | 10/1987 | European Pat. Off. |
| 0330120 | 8/1989 | European Pat. Off. |
| 61-62843 | 3/1986 | Japan |

Primary Examiner—John F. Niebling
Assistant Examiner—Caroline Koestner
Attorney, Agent, or Firm—Fay, Sharpe, Beall, Fagan, Minnich & McKee

[57] ABSTRACT

An electrophoresis pattern reading system of fluorescent type is comprised of a detachable migration unit comprising a gel functioning as a base for electrophoresis and a gel-supporting body for supporting the gel; an electrophoresis unit, to which the migration unit is mounted, for performing electrophoresis by applying migrating voltage to the gel to which a sample labeled with a fluorescent substance is added; and a reading unit including an instrumentation subunit for reading an electrophoresis pattern, to which the migration unit is mounted after electrophoresis and which receives fluorescence emitted from the fluorescent substance of the sample on the gel upon application of light to the gel. For example, a plurality of the migration units and the electrophoresis units are provided, and each of the plural migration units are mounted to one reading unit in order after electrophoresis has been performed with the respective electrophoresis units for a long period of time, thereby reading the electrophoresis pattern in a short period of time.

24 Claims, 8 Drawing Sheets

ELECTROPHORESIS PATTERN READING SYSTEM OF FLUORESCENCE TYPE

BACKGROUND OF THE INVENTION

Field of the Invention

The present invention relates to an electrophoresis pattern reading system of a fluorescence type and, more particularly, to a pattern reader for electrophoresis of fluorescence type, in which detachable migration units are mounted to a plurality of electrophoresis units which are electrophoresed simultaneously with each other, and an electrophoresis pattern is read by a common reader unit, thereby efficiently implementing electrophoresis and reading the electrophoresis pattern.

The pattern reader for electrophoresis of the fluorescence type has the advantage that it does not require dangerous and expensive radioisotopes.

Generally speaking, electrophoresis analysis methods using fluorescence method had been used for analysis of various genetic structures including DNA sequencing (determination of a sequence of bases of the gene), mass spectrometry of proteins such as amino acids and analysis of polymer structures. Such an electrophoresis analysis method involves implementing electrophoresis using a sample of fragments labeled with a fluorescent substance and a distribution pattern developed by electrophoresis is analyzed to thereby analyze the samples.

Description will be made of a DNA sequencing device as a representative example of an electrophoresis pattern reader.

In the DNA sequencing using the DNA sequencing device, a sample of a DNA whose structure is determined is first cut into fragments with a restriction enzyme by controlling reactivity against a chemical reaction specific to a site of each a base and labeling them with a fluorescent substance. The fragments are different in length from each other and have each a particular base selected from four kinds of bases labeled at their cut ends, consisting of adenine (A), cytosine (C), guanine (G) and thymine (T). As the fragmented DNA sample can be separated by electrophoresis in accordance with the length of the fragment, each fragment is separated by means of electrophoresis and radiated with laser light to excite the fluorescent substance labeled on each of the fragments. A measurement of the distribution in intensity of the fluorescence emitted from the fluorescent substance permits the reading of a sequence of bases, thereby determining the structure of the DNA.

FIG. 13 is a view showing an example of the distribution of DNA fragments obtained by electrophoresis. As the distance of migration varies with lengths of DNA fragments (the difference of their molecular weights), the fragments having the same molecular weights gather together as time passes, and in an electrophoresis pattern 70, as shown in FIG. 13, bands 66 are formed so as to correspond to the molecular weights of the DNA fragments. As a whole, the electrophoresis pattern is provided such that the bands 66 are formed in lanes 71, 72, 73 and 74. It is to be noted herein that, as there is the difference in molecular weight by one base or more among the bases A, G, C and T of the fragments, the distances of migration for all fragments are different from the other. Hence, it can be theoretically concluded that the bands 66 in the lanes 71 to 74 are not disposed transversely in a row with each other. For DNA sequening, the pattern of the bands 66 is read for each of the bases, A, G, C and T in the respective lanes 71 to 74 in order from the bottom of the pattern, thereby analyzing the DNA sequence.

The above description has been made of the electrophoresis analysis method using the DNA sequencing for analyzing the sequence of the bases of each DNA as an example. It is to be noted, however, that the electrophoresis method can likewise be applied to analysis of other samples. The electrophoresis of the sample subject to analysis allows the sample to be separated into different molecular weights and to form bands corresponding to the separated molecular weights. Hence, the difference in molecular weight between the components of the sample can be determined by reading the distribution of the bands formed. Furthermore, the electrophoresis may be applied to assumption of a molecular weight of a compound or determination of the presence or absence of a given molecule by measuring the distance of migration of the sample and judgment of the presence or absence of the band in a predetermined position.

By pouring a sample labeled with a fluorescent substance into a gel functioning as a base for electrophoresis and electrophoresing the gel, the gel is provided with a distribution of bands after electrophoresis in accordance with the molecular weights of components of the sample so that the distribution of the bands is measured. A measurement of the band distribution is made by radiating the electrophoresed gel with light such as laser light that generates fluorescence upon excitement of the fluorescent substance, and the distribution pattern of the bands is measured by detecting the fluorescence emitted upon reaction with a photoelectrically converting element.

The electrophoresis device of fluorescence detecting type is described, for example, in Japanese Patent Unexamined Publication (kokai) No. 61-62,843/1986.

Description will now be made of the electrophoresis device of such fluorescence type.

FIG. 9 is a perspective view showing an outlook of a conventional electrophoresis device. As shown in FIG. 9, the conventional electrophoresis device comprises an electrophoresis and instrumentation unit 51 for carrying out electrophoresis and instrumenting the distribution of fluorescence, a data processor unit 52 for processing data instrumented, and a cable 53 connecting them to each other. The electrophoresis and instrumentation unit 51 has a door 51a and the door 51a is opened to pour a gel functioning as a base for electrophoresis of DNA fragments and then a given amount of a sample to be analyzed. Then the door 51a is closed and a switch is turned on to start up electrophoresis. As electrophoresis has been started up, an operational state is displayed and monitored on a display panel 51b of the electrophoresis and instrumentation unit 51. The data instrumented is then transferred to the data processor unit 52 and is subjected to desired data processing in accordance with preset programs. The data processor unit 52 comprises predominantly a main body of a computer 54 consisting of a microprocessor, memory and so on, a keyboard 55 from which instructions are given by the operator, a display 56 for display processing results and states, and a printer 57 for recording the processed results.

FIG. 10 is a block diagram showing the construction of the electrophoresis and instrumentation unit. As shown in FIG. 10, the electrophoresis and instrumentation unit 51 (FIG. 9) comprises an electrophoresis subunit 63 and a signal processor subunit 64. The electrophoresis subunit 63 further comprises an electrophoresis section 5 in which electrophoresis is performed, a first electrode 2a and a second electrode 2b for applying voltage to the electrophoresis section 5, a support plate 3 for supporting the electrophoresis section 5 and the first and second electrodes 2a and 2b, a power supply 4 for electrophoresis for applying voltage to the electrophoresis section 5, a light source 11 for generating light to excite a fluorescent substance, an optical fiber 12 for leading the light from the light source 11, a condenser 14 of an optic system for condensing and collecting fluorescence 13 generated by the fluorescent substance, an optical filter 15 for selectively passing the light having a particular wavelength therethrough, and an optical sensor 16 for converting the condensed light into electrical signals. The signal processor subunit 64 further comprises an amplifier 17 for amplifying the electrical signals from the optical sensor 16, an analog-digital converting circuit 18 for converting analog signals of the electrical signals into digital data, a signal processing section 19 for implementing pre-processing of the digital data converted, for example, by addition average processing or the like, an interface 20 for implementing the interface processing for feeding the pre-processed data to an external data processor, and a control circuit 10 for performing an entire control of the electrophoresis and the signal processing. The digital signal OUT is generated from the signal processor subunit 64 and then supplied to the data processor unit 52 (FIG. 9), thereby implementing the data processing such as analysis processing and so on.

Description will now be made of operation of the electrophoresis device which is constructed in the manner as described hereinabove.

Reference is made to FIGS. 9 and 10. After the door 51a of the electrophoresis and instrumentation unit 51, a gel is poured into the electrophoresis section 5 disposed within the unit 51 and thereafter a sample of DNA fragments labeled with a fluorescent substance is poured thereinto. A switch of the display panel 51b is turned on to give an instruction for starting-up electrophoresis, and then voltage is applied from the first and second electrodes 2a and 2b of the power supply 4 to the electrophoresis section 5, thereby starting up electrophoresis. The electrophoresis allows the sample labeled with the fluorescent substance to be migrated in the lanes 71, 72, 73 and 74, thereby gathering the molecules having the same molecular weights together and forming the bands 66, for instance, as shown in FIG. 13. The molecules having smaller molecular weights are allowed to migrate at a rate faster than those having greater molecular weights so that the former is migrated in a distance longer than the latter within the same time unit. The bands 66 are detected in a manner as shown in FIG. 11a by leading light from the light source 11 through the optical fiber 12 and radiating the gel in the electrophoresis section 5 on its optical path, thereby forcing the fluorescent substance labeled on the bands 66 of the gel to emit fluorescence 13.

Referring to the front view as shown in FIG. 11a and to the longitudinally sectional view as shown in FIG. 11b, the electrophoresis section 5 comprises a gel 5a consisting of polyacrylic amide or the like and support plates 5b and 5c made of glass for supporting and interposing the gel 5a from the both sides. For example, a sample of DNA fragments is poured into the gel 5a of the electrophoresis section 5 from its upper portion and electrophoresis is carried out by applying voltage to the first electrode 2a and the second electrode 2b (FIG. 10).

Light radiated from the light source, for example, laser light, passes through the light path 61 in the gel 5a from the optical fiber 12 and radiated to the fluorescent substance on the light path 61. This allows the fluorescent substance present on the light path 61 to be excited to emit fluorescence 13. The fluorescence 13 emitted is led to a substage condenser 14 of optics consisting of a combination of lenses and then selected by the optical filter 15 after being condensed, thereby converting it into electrical signals by means of the sensor 16. The electrical signals obtained by the sensor 16 is amplified to a desired level by the amplifier 17 and subjected to analog-digital conversion by the analog-digital circuit 18 followed by a supply to the signal processing section 19. The signal processing section 19 processes the signals by means of addition-average processing or the like in order to improve a signal-noise ratio. The data of the digital signals which has been subjected to signal processing is fed to the data processor subunit 52 through the interface 20.

FIGS. 12a and 12b are views describing an embodiment of fluorescence intensity pattern signals of the DNA fragments to be transferred from the electrophoresis and instrumentation subunit 51. For instance, as shown in FIG. 12a, as the laser light is radiated upon the electrophoresis section 5 in which the electrophoresis is performed, the fluorescent substance of the gel present on the light path 61 is excited to emit fluorescence 13. This fluorescence 13 is detected in predetermined detection positions in each lane in the direction of electrophoresis in the course of lapse of time. This allows the fluorescence 13 to be detected when the bands 66 in each lane pass through the positions on the light path 61, thereby detecting a pattern signal of fluorescence intensity in each lane, as shown in FIG. 12b. Therefore, the pattern signal of the magnitude of fluorescence intensity as shown in FIG. 12b is represented as a pattern signal of fluorescence intensities of the bands 66 in the electrophoresis direction 62. The data processor unit 52 performs data processing for comparing molecular weights and determining the sequence of DNA from data of the pattern of fluorescence intensity. The sequence of the bases or the like determined by data processing is symbolized and then generated, thereby being displayed on a display screen 56 or printed by a printer 57. The data of the result obtained by data processing may be recorded in magnetic recording media as needed. It is to be noted that the time period required for electrophoresis by the pattern reader for electrophoresis having the construction as described hereinabove ranges usually from 5 to 8 hours in the case of electrophoresis of DNA fragments and the time period for reading the distribution of the fluorescent substances in the electrophoresed gel. Hence, it is the current situation in which the analyzer for the electrophoresis method such as the DNA sequencer is occupied for most of its treating time by electrophoresis once the processing for analyzing the substance has been started up. The data processor unit for data processing of the results read from the electrophoresis pattern, which is to be used together with the analyzer for the electrophoresis method of this kind, is constructed as a separate unit so as to allow a general-purpose data processor to be utilized therefor. The electrophoresis and instrumentation unit in which electrophoresis is performed and the electrophoresis pattern is read is an integral combination of an electrophoresis subunit which performs electrophoresis and a signal processor subunit which implements data processing by reading the band pattern as a result of electrophoresis. Hence, once electrophoresis for one sample has started up, the electrophoresis and instrumentation unit is occupied for a long period of time for a series of analyzing processes in which the pattern is read. More specifically, as described hereinabove, for the conventional electrophoresis pattern reading system, the electrophoresis and instrumentation unit has been occupied for the total period of time of about 5-8 hours for electrophoresis and 30 minutes for reading the distribution of the fluorescent substance developed in the gel, so that it is the problem that the expensive system cannot effectively be used.

SUMMARY OF THE INVENTION

The present invention has the object to provide an electrophoresis pattern reading system of fluorescent type in which the electrophoresis pattern is efficiently read by the fluorescence method and the system can effectively be utilized.

The present invention has another object to provide a method for reading an electrophoresis pattern, in which electrophoresis can be performed by using the electrophoresis pattern reading system of fluorescent type and a pattern of distribution of the fluorescent substance electrophoresed can effectively read.

The present invention has a still further object to provide an electrophoresis pattern reading system of fluorescent type, which is constructed such that an electrophoresis unit for performing electrophoresis of fragments of a sample labeled with a fluorescent substance is disposed separated from a reading unit for reading the distribution of the fluorescent substance as a result of electrophoresis and in which the gel as a result of electrophoresis obtained by using a plurality of plural electrophoresis units is read with the same reading unit, thereby reading the electrophoresis pattern efficiently.

In order to achieve the objects, the present invention consisting of the electrophoresis pattern reading system of fluorescent type is characterized by a detachable migration unit consisting of a gel functioning as a base for electrophoresis and a gel-supporting body for supporting the gel; an electrophoresis unit to which the migration unit is mounted and in which electrophoresis is performed by applying the migrating voltage to the gel to which a sample labeled with a fluorescent substance is added; and a reading unit to which the migration unit is mounted after electrophoresis and in which the electrophoresis pattern is read by irradiating the gel with light and receiving fluorescence generated from the fluorescent substance of the sample on the gel. By providing the detachable migration unit comprised of the gel functioning as the base for electrophoresis and the gel-supporting body for supporting the gel, the electrophoresis pattern reading system of fluorescent type is of a separate structure in which the electrophoresis unit having the migration unit for electrophoresis is disposed separately from the electrophoresis pattern reading unit with the migration unit mounted after electrophoresis. Hence, the electrophoresis unit in which electrophoresis is performed for a long period of time is of such a structure as being separate from the electrophoresis pattern reading unit which performs reading the electrophoresis pattern in a relatively short period of time, thereby enabling the electrophoresis unit to be separated from the operation of the reading unit by using the detachable migration unit composed of the gel functioning as the base for electrophoresis and the gel-supporting body for supporting the gel. This can avoid an expensive electrophoresis pattern reading system of fluorescent type as a whole from being occupied for a long period of time. The expensive reading unit having a complicated and highly sophisticated processing mechanism can now be shared with a plurality of the electrophoresis units prepared at cheaper costs. This arrangement can also allow electrophoresis to be performed simultaneously with a plurality of the electrophoresis units and enables the common reading unit to read the results of electrophoresis in order, thereby resulting in an efficient analysis of samples by electrophoresis. As described hereinabove, by using the detachable migration unit composed of the gel functioning as the base for electrophoresis and the gel-supporting body for supporting the gel, which is mounted to the electrophoresis unit, electrophoresis can be performed by adding the sample labeled with the fluorescent substance to the gel. After electrophoresis has been finished, the migration unit is detached from the electrophoresis unit and the migration unit is then mounted to the reading unit after electrophoresis after the gel is removed from the electrophoresed migration unit or while the gel is held while being supported by the gel-supporting body and, if necessary, the gel is colored with a colorant or the gel is dried. In the reading unit, the fluorescent substance on the gel in the migration unit is irradiated with light and the distribution of the fluorescent substance on the gel is optically read and recorded as image data by a recording medium such as paper, film, magnetic recording medium or the like. Parallel and simultaneous electrophoresis of different samples under different conditions using a plurality of migration units which are mounted to a plurality of electrophoresis units permits the migration units one after another subsequent to completion of electrophoresis to be mounted to the reading unit and the distribution data of the fluorescent substances in the gel to be read in order, thereby resulting in an efficient reading of electrophoresis patterns. Therefore, the electrophoresis pattern reading system of fluorescence type can be arranged, for example, such that a plurality of researchers share the reading unit and each of them owns its own electrophoresis unit. This system enables an efficient electrophoresis analysis by allowing each of the researchers to perform electrophoresis with its own electrophoresis unit, to mount the resulting migration unit to the common reading unit, and to read the results (gels) of electrophoresis by means of the common reading unit. This system can result in an economical construction of, for example, an automatic DNA analyzing system. It is further to be noted that the gel in the migration unit can manually be analyzed, without the use of a digital analyzer, directly from information on transcription which may be obtained by transcribing the original data on distribution of the fluorescent substance, obtainable by radiation of the gel with light, to the recording medium as its intact image. This permits the efficient reading processing of the electrophoresis pattern.

DESCRIPTION OF THE PREFERRED EMBODIMENTS

Figure 1:
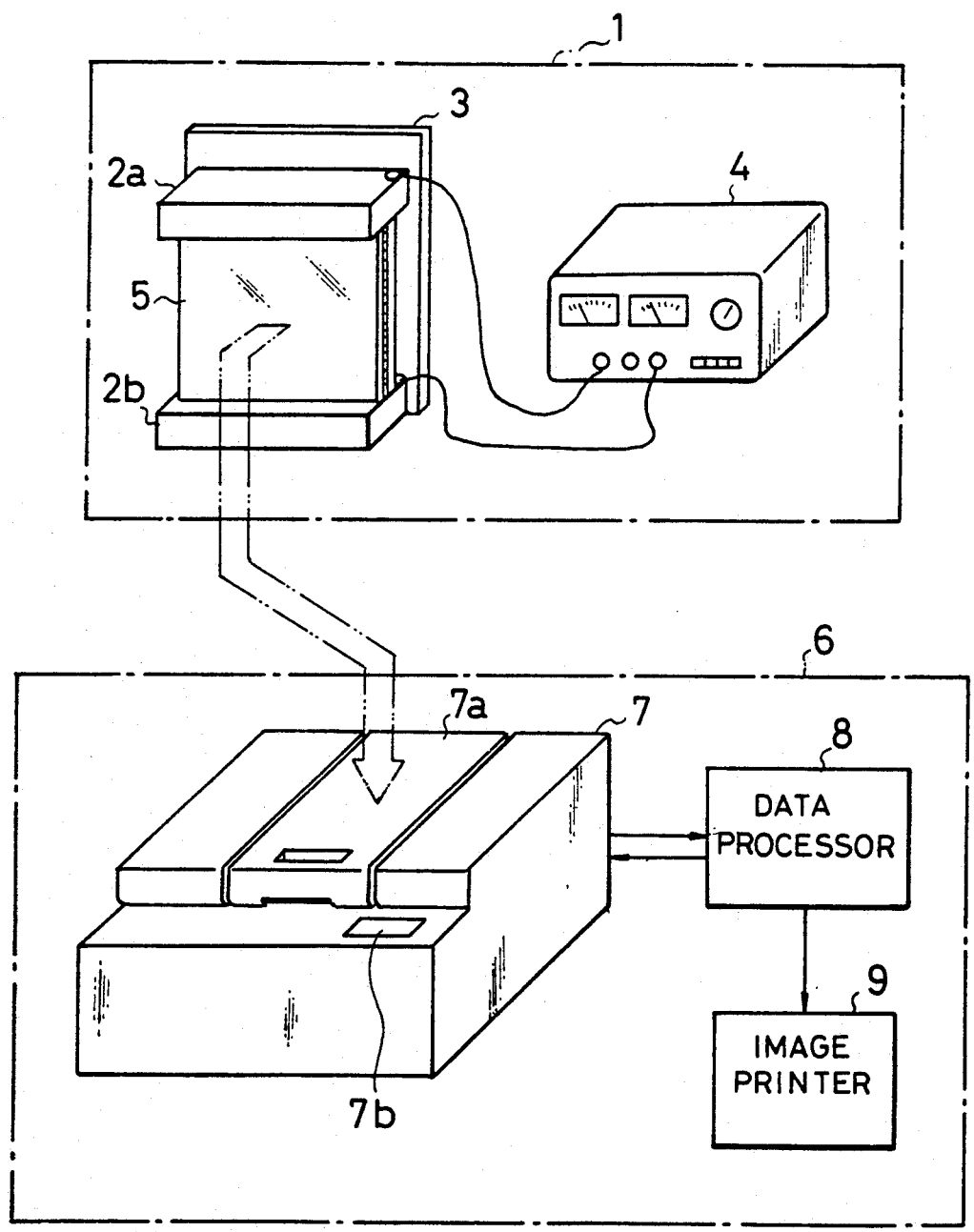
FIG. 1 is a diagrammatic representation of an overall construction of the electrophoresis pattern reading system of fluorescent type according to an embodiment of the present invention.
Figure 11A:
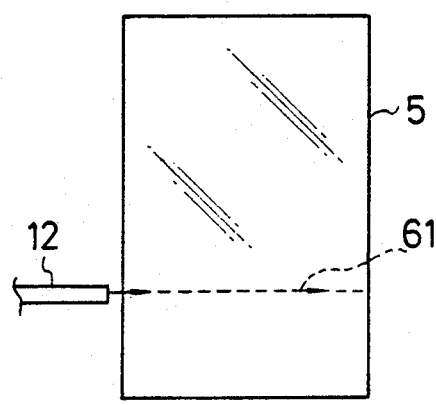
FIGS. 11a and 11b are views showing the operational principle of detecting the electrophoresis pattern by the fluorescence method.
Figure 11B:
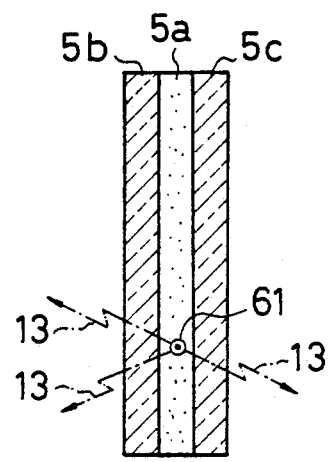
Figure 12A:
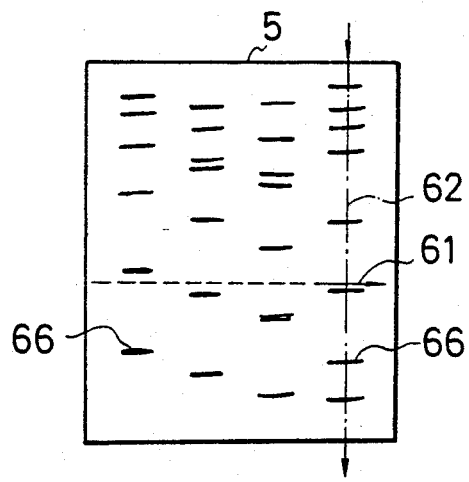
FIGS. 12a and 12b are views showing examples of pattern signals for fluorescence intensity of DNA fragments to be fed from the instrumentation unit 41.
Figure 12B:
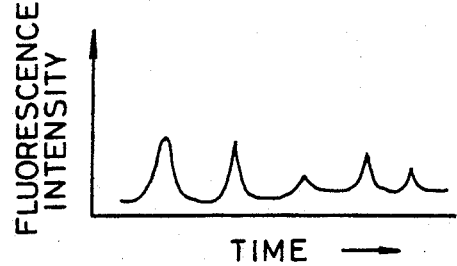

FIG. 1 diagrammatically represents the overall construction of the electrophoresis pattern reading system of fluorescent type according to an example of the present invention. As shown in FIG. 1, the electrophoresis pattern reading system of fluorescent type is overall constructed such that an electrophoresis unit 1 is disposed separately from a reading unit 6. The electrophoresis unit 1 comprises a migration subunit 5 composed of a gel functioning as a base for electrophoresis and a gel-supporting body for supporting the gel, a first electrode 2a and a second electrode 2b for applying electrophoresis voltage to the migration subunit 5 (hereinafter referred to as migration section) mounted, a supporting plate 3 for supporting the first electrode 2a and the second electrode 2b as well as the migration section 5, and a power supply 4 for electrophoresis for supplying the electrophoresis voltage. The migration section 5 comprises the gel such as polyacrylamide or the like on which a sample for electrophoresis is developed and the gel-supporting body such as glass plates disposed so as to interpose the gel from the both sides, as describe hereinabove (as shown in FIGS. 11a and 11b). In the electrophoresis unit 1, the migration section 5 is mounted and a sample of fragments subject to electrophoresis is supplied from an upper portion of the gel in the migration section 5. Thereafter, the migration voltage is applied to the first electrode 2a and the second electrode 2b from the power supply 4 for electrophoresis, thereby starting up electrophoresis After electrophoresis, the migration section 5 is removed from the electrophoresis unit 1 and then mounted to the reading unit 6.

The reading unit 6 is to perform data processing by mounting the migration section 5 after electrophoresis as it is (or in such a state of the gel that is removed from the migration section 5). As shown in FIG. 1, the reading unit 6 is composed of an instrumentation subunit 7 as a major component and a data processor unit 8 and an image printer 9 are added thereto. The data processor unit 8, the image printer 9 and so on are arranged so as to generate the electrophoresis pattern data read by the instrumentation subunit 7 after data processing, image processing and judgment processing. To the instrumentation subunit 7 is the migration unit 5 (the migration unit composed of the gel and the gel-supporting body) after electrophoresis has been performed in the electrophoresis unit 1, and a reading base is disposed immediately underneath a lid 7a at an upper portion of the instrumentation subunit. The migration section 5 removed from the electrophoresis unit 1 is mounted to the reading base of the instrumentation subunit 7 electrophoresis unit 1 by opening the lid 7a. After the migration section 5 with the gel as the object for reading has been mounted, the lid 7a is closed and a switch on an operational display panel 7b for starting up the reading operation is then pressed, whereby the instrumentation subunit 7 starts up the reading of the electrophoresis pattern of the gel of the migration section 5. As the reading of the electrophoresis pattern starts up, the light from the light source equipped in the instrumentation subunit 7 is scanned and the gel of the migration section 5 mounted is irradiated with exciting light to excite the fluorescent substance and the distribution of the fluorescent substance is instrumented by receiving the fluorescence. The data processor unit 8 is to process data on the basis of the read data that has been instrumented by the instrumentation subunit 7 and to control the instrumentation subunit 7. The data processed is visualized by the image printer 9 or the like.

Figure 2:
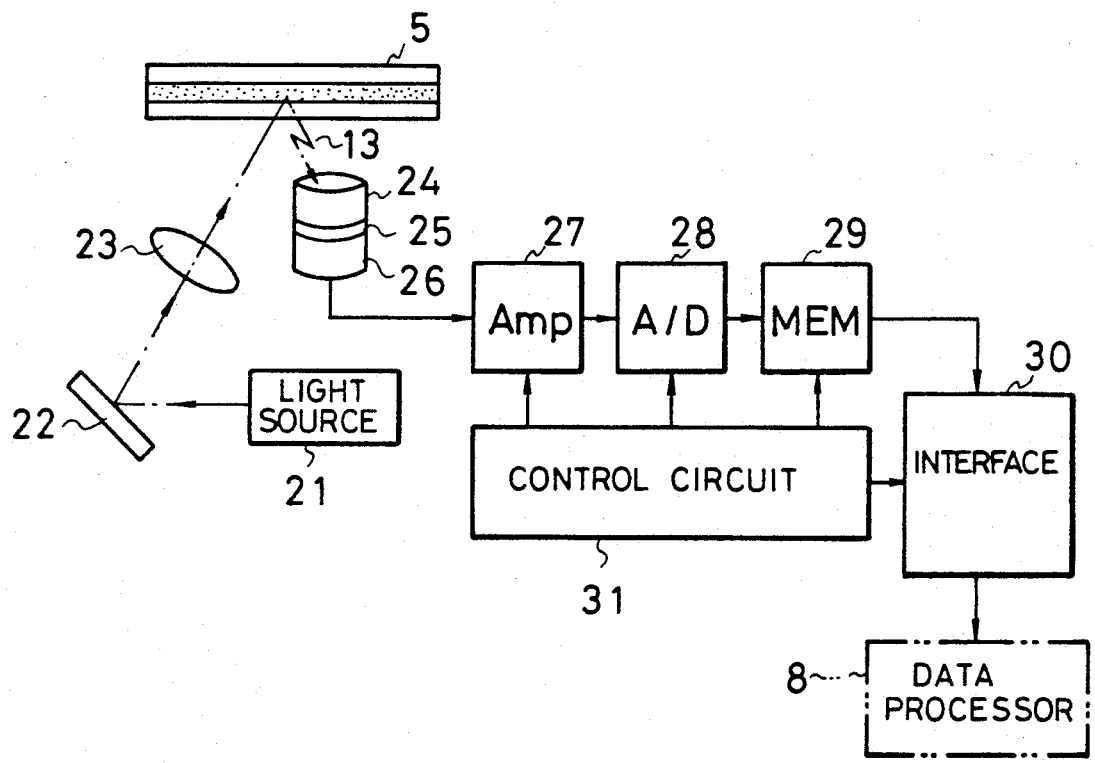
FIG. 2 is a block diagram showing the construction of an essential portion of an instrumentation unit.
Figure 3:
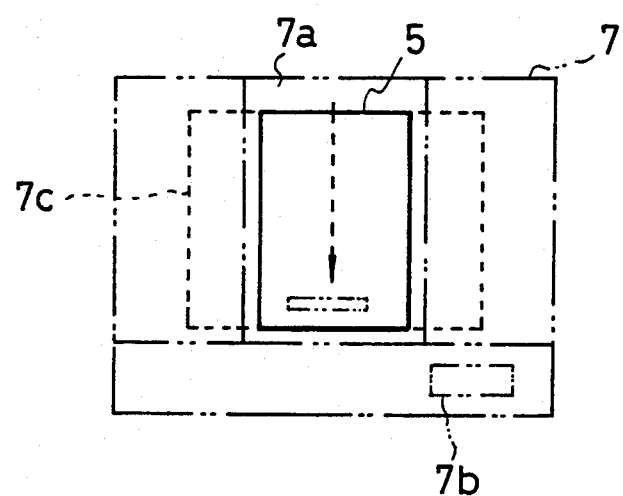
FIG. 3 is a view showing the position in which the migration unit to be mounted to the instrumentation unit is mounted.

FIG. 2 is a block diagram showing the construction of the essential portion of the instrumentation subunit, and FIG. 3 is a view showing the position in which the migration section is mounted to the instrumentation subunit.

Description will be made with reference to FIGS. 2 and 3.

In performing electrophoresis analysis of a sample by using the electrophoresis pattern reading system, the sample labeled with the fluorescent pigment is first subjected to electrophoresis using electrophoresis unit 1. After electrophoresis for a given period, the migration section 5 is removed from the electrophoresis unit 1. Thereafter, the gel of the migration section 5 removed is placed on an upper portion of the reading base 7c in the instrumentation subunit 7 after opening the lid 7a of the reading unit 6 at the upper portion of the instrumentation subunit 7 in such a state that the migration section 5 is as it is after removal or that glasses of the gel-supporting body are removed, as shown in FIG. 3. Then the lid 7a is closed. This concludes the setting to the instrumentation subunit 7. At this time, if the gel after electrophoresis is not yet labeled with the fluorescent pigment, the processing for labeling the sample with the pigment is executed. Further, the processing of drying the gel is also executed.

The operation of giving an instruction of the start-up of reading the electrophoresis pattern will now be performed. The operation of starting the reading is executed by giving a start-up instruction by means of pressing the switch of the operation display panel 7b for starting the reading or from the data processor unit 8. In starting the operation of reading by the data processor unit 8, the state in which the migration unit is mounted to the instrumentation subunit 7 is fed to the data processor unit 8 through a control signal line, and the operation of the instrumentation subunit 7 is controlled by the data processor unit 8 in accordance with the state. In this case, the operation of starting up the reading is automatically executed, thereby reducing the burden of operating the switch on the side of the operator.

The distribution data of the fluorescent pigment read is transferred to the data processor unit 8. The data processor unit 8 executes desired processings such as processing of detecting peaks of fluorescent intensity, processing of determining the migration distance, etc., in accordance with preset programs. The result data obtained by data processing is printed out, as needed, by the image printer 9 as image of the fluorescent intensity with light and shade or as image in which the fluorescent intensity is grouped by contour lines or by colors or the strength of color. The image printed out as the light-and-shade picture in accordance with the fluorescent intensity is the same image as radioactive X-ray film image which has conventionally been used. The result data which has been data-processed is stored, as needed, as digital data by a magnetic or optical recorder.

In the block diagram of FIG. 2 showing the construction of the instrumentation subunit, laser beams generated from a light source 21 are scanned by a vibration mirror 22 in the direction of the front and rear sides of this drawing, collected by a lens 23, and led to the gel of the migration section 5 as the object of reading. The laser beams scanned by the vibration mirror 22 and collected by the lens 23 are focused on the gel in the migration section 5. This allows the fluorescent substance on the light path of the laser beams scanned to be excited, thereby emitting fluorescence 13. The fluorescence 13 is collected by a condenser 24, together with exciting light scattered and so on, and converted into electrical signals by an optical sensor 26 through an optical filter 25. As the condenser 26 are a lens, a conical cylinder, an optical fiber, etc, and they serve as enhancing sensitivity of detecting the fluorescence received with respect to external light. The optical filter 25 is to selectively transmit the wavelength component of the fluorescence, thereby excluding the influence of the scattered exciting light upon the fluorescence received. As described hereinabove, the condenser 24 and the optical filter 25 enhances the sensitivity of receiving the fluorescence to be detected, and the fluorescence received is converted into electrical signals by the optical sensor 26. In order to further enhance the sensitivity of detecting the fluorescence, a photomultiplier having high efficiency of photo-electrical conversion is used as the optical sensor 26. The electrical signals obtained by the optical sensor 26 are amplified by an amplifier 27, and the amplified electrical signals are provided to an analog-digital converting circuit 28 and converted into digital data. The fluorescence-detecting signal converted into the digital data is stored by a memory 29, and the data stored in the memory 29 is supplied to the data processor unit 8 through an interface circuit 30. Overall control of such a series of signal processings is performed by a control circuit 31.

FIGS. 4a, 4b, 4c, 4d and 4e are diagrammatic representations showing the scanning for reading the migration unit mounted to the instrumentation subunit.

Figure 4A:
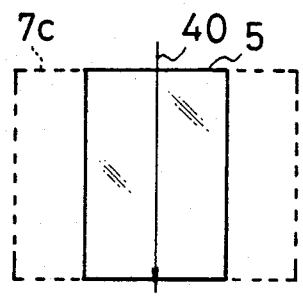
FIGS. 4a, 4b, 4c, 4d and 4e are views showing the scanning for reading the migration unit to be mounted to the instrumentation unit.
Figure 4B:
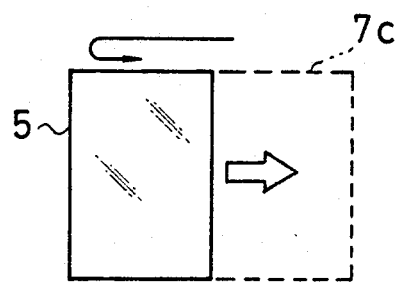
Figure 4C:
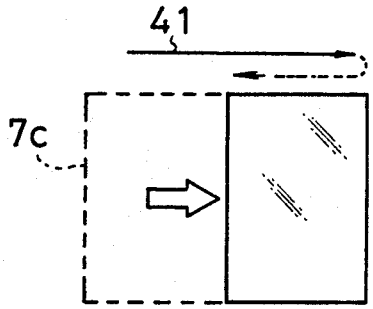

Description will be made of the scanning for reading the migration section 5 (migration unit) as an object of reading, in conjunction with FIGS. 4a–4e. As shown in FIG. 3, the migration unit (migration section 5) as the reading object is mounted to the instrumentation subunit 7 and the migration section 5 mounted is transferred to the left and right on the reading base 7c once the operation of starting the reading has started up, thereby reading the electrophoresis pattern of the gel. The migration section 5 is first set in the position in such a state as shown in FIG. 4a. As shown in FIG. 4a, arrow 40 stands for the direction of scanning the laser beams from the light source, namely, the first scanning direction (main scanning direction). During the reading operation, the migration section 5 is transferred to the left end of the reading base 7c as shown in FIG. 4b, thereby starting up scanning the laser beams in the main scanning direction. The migration section 5 is read while being transferred to the right from the left end at a given speed. The reading finishes as the migration section 5 reaches the right end as shown in FIG. 4c after the migration section 5 has started up being read and transferred to the right at the given speed. In the reading base 7c, the direction in which the arrow 41 is moved at the stage of transferring the migration section 5 is a second scanning direction (sub-scan direction). As described hereinabove, as a result, the distribution of the fluorescent substance on the gel in the migration section 5 is read as a two-dimensionally distributed image.

Figure 4D:
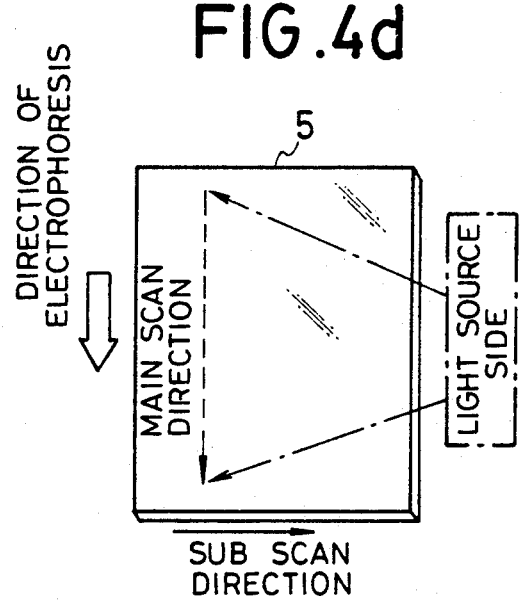
Figure 4E:
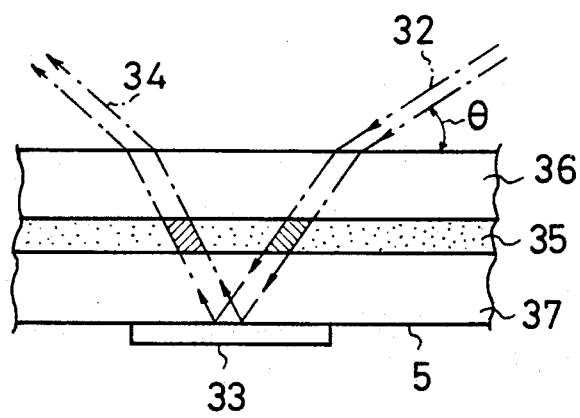
Figure 13:
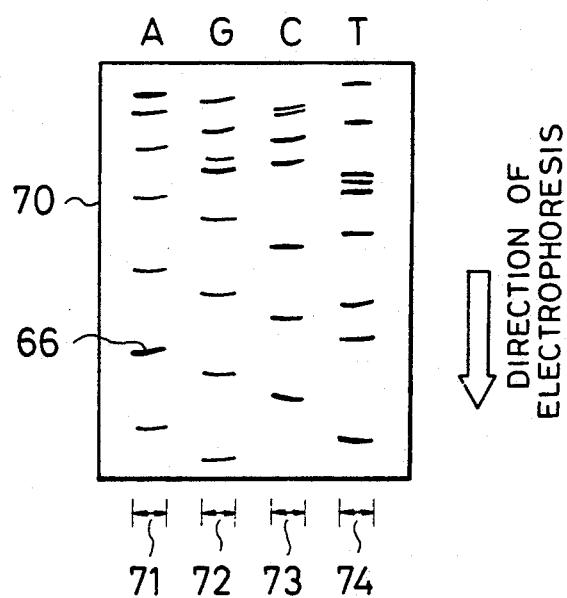
FIG. 13 is a view showing an example of the distribution of electrophoresed DNA fragments.

In the two-dimensional reading operation by means of the relative transfer of the migration section 5 in the manner as described hereinabove, the scanning of the laser beams by the reading light is equivalent of reading by scanning the surface of the migration section 5 in both the main scan direction (the scanning direction indicated by the arrow 40) and the sub-scan direction (the scanning indicated by the arrow 41), as shown in FIG. 4d. In this case, the reading is performed in such a manner that the main scan direction is set to a direction that is the same as the direction of electrophoresis. In scanning for reading in the manner as described hereinabove, it is to be noted that the longitudinal direction is read in the same size as the transverse direction when the speed for scanning the first scanning direction (main scan direction) is set to the same as that for scanning the second scanning direction (sub-scan direction). It is noted, however, that a pattern of electrophoresis bands of the gel in the migration section as the object for reading is such that bands expand in a band-like form in the direction normal to the electrophoresis direction, as shown in FIG. 13, so that, when the sequence of bases is given, the resolving ability for reading in the direction (the first scanning direction) parallel to the direction of electrophoresis is highly required. On the contrary, the resolving ability for reading in the second scanning direction is sufficient even if it would be lower than that for reading in the first scanning direction. Hence, in this reading operation, the main scan direction is set to the same direction as the electrophoresis direction, as shown in FIG. 4d, and the exciting light is applied to the fluorescent substance in the gel 35 by leading light 3 from the light source to the reading surface of the migration section 5 at a given incidence angle $\theta$, as shown in FIG. 4e. A mirror 33 is disposed on the side opposite to the incidence side of the light 32, and light is additionally provided to the fluorescent substance of the gel 35 as light 34 reflected from the mirror 33. The light 32 entering glass 36 of the migration section 5 is transmitted through glass 37 disposed on the side opposite to the gel 35 and reflected on the mirror 33 and then transmitted again through the glass 37, the gel 35 and the glass 36, thereafter resulting in reflected light 34 toward the outside. This arrangement can improve the reading speed in the second scanning direction by enlarging the area by giving the exciting light to the fluorescent substance as a result in the second scanning direction.

Figure 5A:
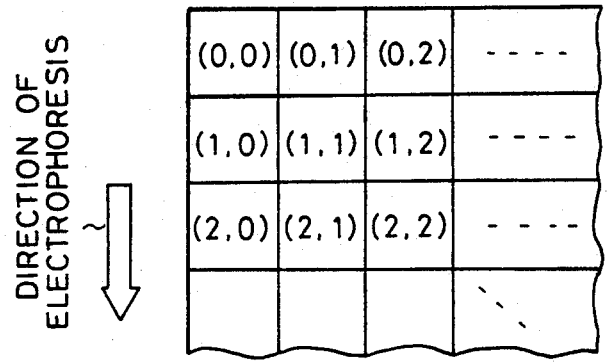
FIG. 5a is a view showing an example of pixel data to be obtainable when no reflecting light is used for scanning with reading light.
Figure 5B:
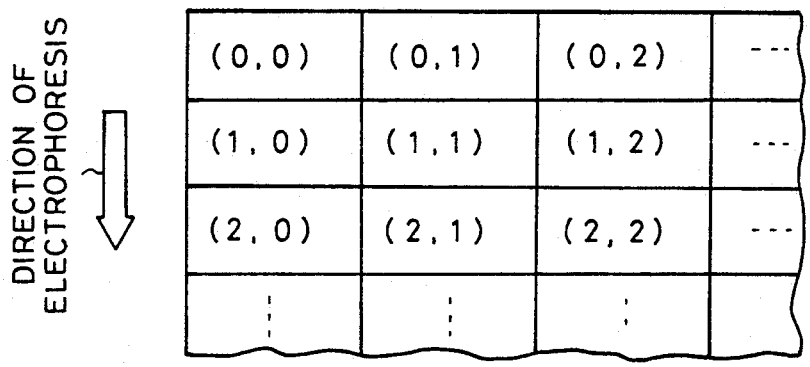
FIG. 5b is a view showing an example of pixel data to be obtainable when reflecting light is used for scanning with reading light.

FIG. 5a is a view showing an example of pixel data to be obtained in an instance where no reflected light is used for scanning the reading light, and FIG. 5b is a view showing an example of pixel data to be obtainable in an instance where reflected light is used for scanning the reading light. By lowering the resolving power for detecting the fluorescent substance of the gel in the second scanning direction by using the reflected light for scanning the reading light, the pixel data to be obtained is a pixel data to be read with respect to a pixel size in the region as large as two times the pixel size in the second scanning direction (in the direction crossing at a right angle to the direction of electrophoresis), as shown in FIG. 5b. The method for reading in the manner as described hereinabove enables the reading speed to become high while maintaining the resolving power of reading in the first scanning direction, which is required for determination of the sequence of bases.

Figure 6A:
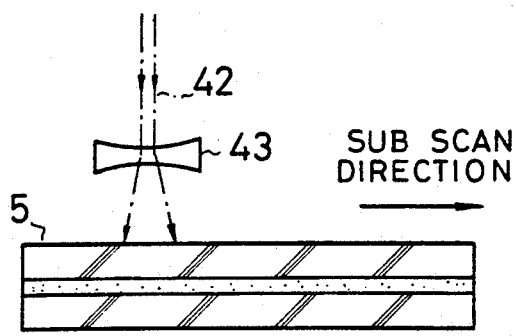
FIGS. 6a and 6b are views showing another example of the reading method with enlarged resolving power by enlarging the size of pixels for reading a fluorescent substance in a given direction.
Figure 6B:
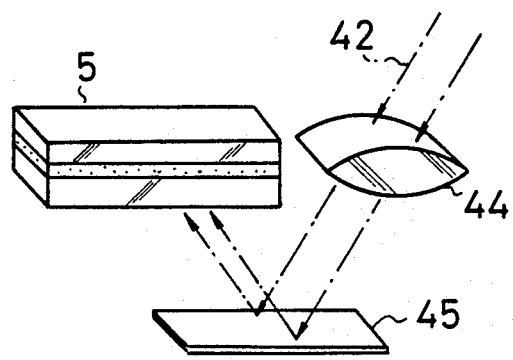

FIGS. 6a and 6b represent other examples of the method for reading to enhance the reading speed by enlarging the pixel sizes of the fluorescent substance in the given direction.

As shown in FIG. 6a, for example, the other first method is a method for applying the exciting light 42 from the light source to the migration section 5 by enlarging the reading pixel size by means of a cylindrical lens 43 having a concave lens form in section in the sub-scan direction (second scanning direction) so as to become longer with respect to the direction perpendicular to the sub-scan direction in order to enlarge the reading pixel size with respect to the sub-scan direction (second scanning direction).

In the instance as described hereinabove, description has been made of the case where the main scan direction (first scanning direction) is the same direction as the direction of electrophoresis. In instances, however, where the main scan direction is perpendicular to the direction of electrophoresis, the reading speed can be made higher by enlarging the reading pixel size of the fluorescent substance in a given direction. In this case, as shown in FIG. 6b, there is used the cylindrical lens 44 in a convex form in section. In other words, in instances where the main scan direction is perpendicular to the direction of electrophoresis, the cylindrical lens 44 in the convex form in section is disposed in the direction nearly parallel to the direction of electrophoresis. Likewise, as shown in FIG. 4e, it is possible to change the reading speed by varying the pixel size for reading with a ratio of the longitudinal light spot size to the transverse light spot size by changing the angle of incidence of the exciting light 42, the location of the cylindrical lens 44, and so on. Further, where it is acceptable if the resolving power in the second scanning direction would be lower than that in the first scanning direction, the data processing for the read pixel data is performed by thinning out the pixel data in the transverse direction which is the second scanning direction, namely, by thinning out the scanning position by one or more pixel data. This permits the processing of the pixel data at a high speed, which follows.

Description will be made of variants of examples.

In the above description on the examples, the scanning method is adopted in which laser beams are scanned for reading using the vibration mirror 22 in the instrumentation subunit 7. There may also be used the method using a polygonal mirror or the scanning method in which the direction of the axis of light is changed by using the optical characteristics such as refraction, interference and so on. The use of an image sensor or an array sensor as the optical sensor for detecting the fluorescence emitted for scanning by the exciting light applied to the migration segment permits part of the reading scanning to be performed electronically, thereby simplifying a scanning mechanism by scanning laser beams for reading by scanning.

Figure 7:
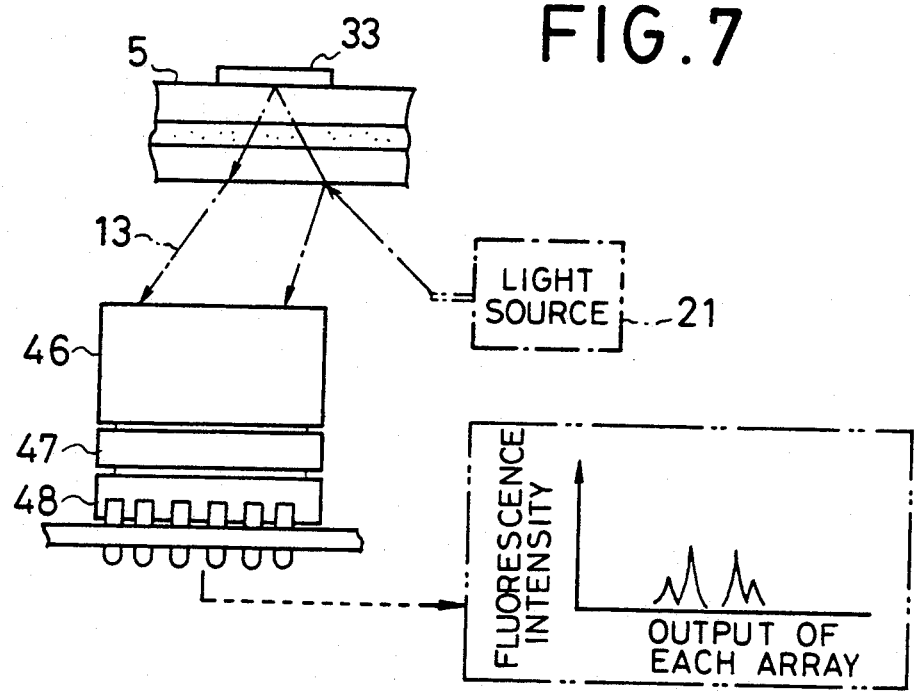
FIG. 7 is a diagrammatic representation showing the construction of an essential portion in which a one-dimensional sensor of an image sensor of semiconductor device is used as a light receiving section for detecting fluorescence from the migration unit.

FIG. 7 is a diagrammatic representation of an outline of the construction showing the essential portion in which a one-dimensional sensor of the image sensor of a semiconductor device as the optical sensor for the light-receiving section for detecting fluorescence from the migration segment. As shown in FIG. 7, fluorescence 13 emitted upon receipt of light for excitement from the light source 21 is condensed by the condenser 46 and led to an image sensor 48 of a static induction transistor type after transmitting through the optical filter 47, thereby converting the fluorescence into electrical signals. The image sensor 48 of the static induction transistor type is suitable for receiving a slight degree of fluorescence caused by a noise by a dark current as low as several orders. Further, a one-dimensional image sensor of a CCD sensor cooled may provide a light-receiving section of a likewise high sensitivity.

As described hereinabove, by using the one-dimensional image sensor as the optical sensor of the light-receiving section to be used for reading the fluorescence, the scanning in the main scanning direction can be executed electronically, thereby simplifying the scanning mechanism for reading. The use of the one-dimensional sensor can allow the scattered light 13a of the exciting light emitted on the glass surface of the migration section 5 to separate the component transmitted through the optical filter 47 from the component of the fluorescence 13 from the fluorescent substance in a physical position, thereby extracting only the component of the fluorescence 13 effectively and improving a ratio of the signal for detecting the signal for the fluorescence intensity pattern to noise. This specifically can improve the limit of detecting the fluorescent signal by one order or more.

Figure 8:
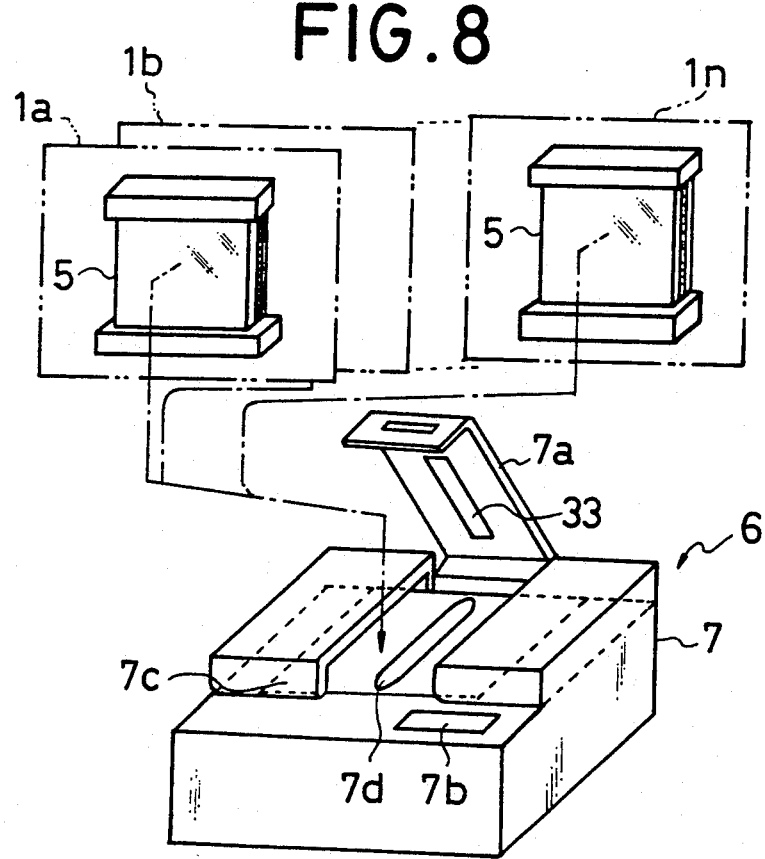
FIG. 8 is a view showing the reading method for reading the electrophoresis pattern by using the electrophoresis pattern reading system of fluorescent type according to an example of the present invention.
Figure 9:
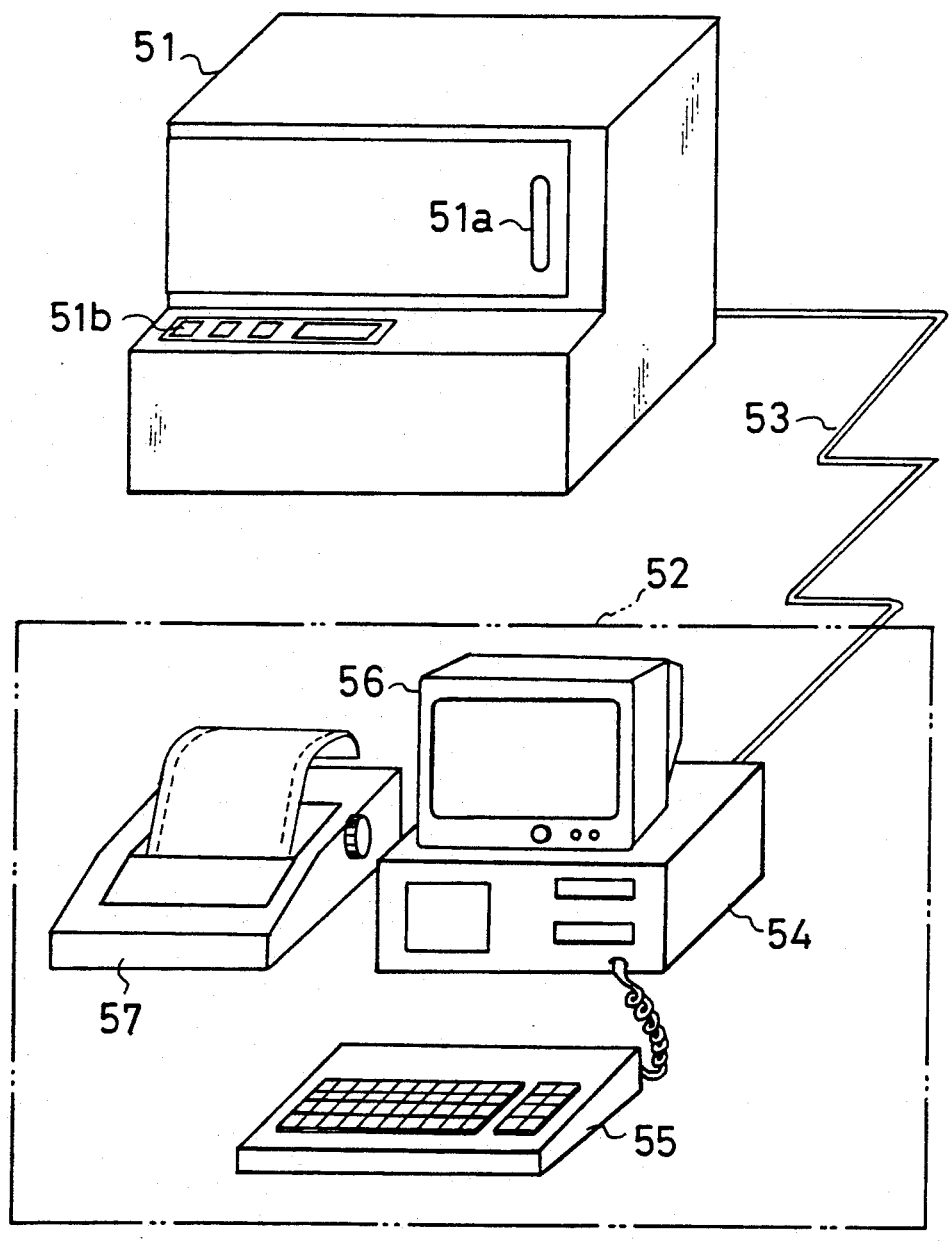
FIG. 9 is a perspective view showing an appearance of the electrophoresis unit.
Figure 10:
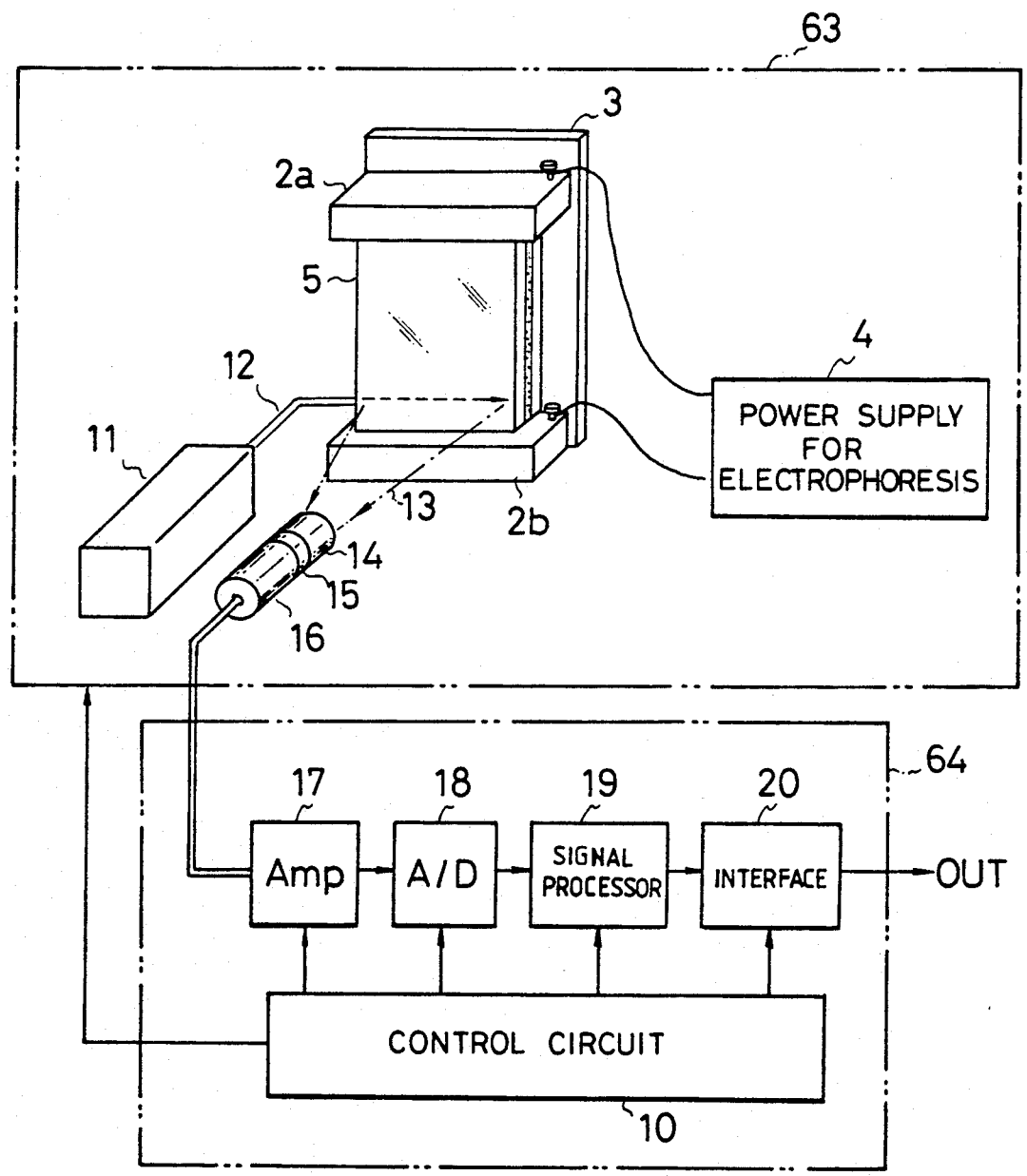
FIG. 10 is a block diagram showing the construction of the instrumentation unit.

FIG. 8 is a diagrammatical representation for describing the reading method for reading the electrophoresis pattern by using the electrophoresis pattern reading system of fluorescent type according to an embodiment of the present invention. As shown in FIG. 8, this embodiment uses the electrophoresis pattern reading system of fluorescent type composed of plural electrophoresis units $1a, 1b, \ldots, 1n$ and one reading unit 6 (instrumentation subunit 7). The migration sections 5 are mounted to the plural electrophoresis units $1a, 1b, \ldots, 1n$, and each of the migration sections 5 is subjected to electrophoresis for an analyzing sample. After electrophoresis, the migration sections 5 are removed from the electrophoresis units $1a, 1b, \ldots, 1n$ and they are mounted in order to the instrumentation subunit 7 of the reading unit 6 for reading the electrophoresis pattern. Although not shown in FIG. 8, the data processor unit (8; FIG. 1) is connected to the instrumentation subunit 7 of the reading unit 7, so that the data processor unit 7 processes data in order for analysis of the sample from the electrophoresis pattern read. In this case, a conventional electrophoresis device can be used as an electrophoresis unit and the electrophoresed gel is mounted to the reading unit 6 and the pattern of bands on the gel can be read.

As described hereinabove, electrophoresis starts up after preparing for a sample to be analyzed and setting it to each of the migration sections 5 which in turn are mounted to the electrophoresis units 1a, 1b, . . . , 1n. Electrophoresis requires about 5 to 8 hours. After electrophoresis has been finished, the migration section 5 is removed from the electrophoresis unit and mounted to the instrumentation subunit 7 of the reading unit 6 to measure the distribution of the fluorescent substance. The migration section 5 is placed on the reading base 7c, the lid 7a is closed, and the switch of the display-operating panel 7b is pressed to generate laser output from the window 7d for reading and to scan the migration section 5 set. The reading time required is about 0.5 hours for reading a 300 mm × 400 mm region.

Therefore, each researcher can implement electrophoresis by exclusively using the electrophoresis unit and read the electrophoresis pattern using the common reading unit. This arrangement can effectively use each of the units without occupying the expensive electrophoresis system of fluorescent type as a whole for a long period of time.

The embodiments according to the present invention as described hereinabove including the variants and applications can be summarized as follows:

(1) The electrophoresis pattern reading system of fluorescent type is comprised of a separate combination of the electrophoresis unit and the reading unit. Electrophoresis is performed by using the migration unit comprised of the gel functioning as a base for electrophoresis and the gel-supporting body for supporting the gel and mounting the migration unit to the electrophoresis unit. After electrophoresis has been finished, the migration unit is removed from the electrophoresis unit and mounted to the reading unit. In the reading unit, the gel in the migration unit is irradiated with light for exciting the fluorescent substance and the fluorescence emitted from the fluorescent substance of the sample on the gel is received to read the electrophoresis pattern. The electrophoresis unit is provided with the power supply for applying the migrating voltage for electrophoresis to the gel into which the sample labeled with the fluorescent substance is poured.

(2) One reading unit can be provided with a plurality of the electrophoresis units. In other words, the electrophoresis units can be provided in the number more than the reading units.

(3) In reading the electrophoresis pattern by using the electrophoresis pattern reading system of fluorescent type, the migration unit comprised of the gel-supporting body for supporting the gel is mounted to the electrophoresis unit and, after electrophoresis has been finished, the migration unit is removed from the electrophoresis unit and mounted to the reading unit, thereby reading the electrophoresis pattern.

(4) The plural migration units electrophoresed by plural different electrophoresis units are mounted in order to the common reading unit and each of the electrophoresis patterns of the gel in the migration unit is read.

(5) The reading unit is provided with a spot light source for generating light for exciting fluorescence of the fluorescent substance, a scanning section (a vibration mirror, a lens and so on) for scanning the light from the spot light source in the direction nearly parallel to the direction electrophoresis by radiation upon the gel, and a reading section having a light-receiving subsection for receiving the fluorescence from the fluorescent substance.

(6) The light-receiving subsection is composed of a light-receiving unit of a one-dimensional image sensor. The direction in which the light is received is nearly parallel to the direction of electrophoresis.

(7) When the direction nearly parallel to the direction of electrophoresis is set as a first direction and the direction perpendicular to the direction of electrophoresis is set as a second direction, the electrophoresis pattern is read by making the pixel size for reading the gel after electrophoresis longer in the first direction than in the second direction.

(8) When the direction nearly parallel to the direction of electrophoresis is set as a first direction and the direction perpendicular to the direction of electrophoresis is set as a second direction, data of a pattern of distribution of the fluorescent substance is obtained by reading the electrophoresis pattern while thinning out the distance equivalent of one pixel or more in the second direction.

(9) In irradiating the gel with light from the spot light source, light is used for the reading unit, whose width in the direction perpendicular to the direction of electrophoresis is extended by equal times to ten and several times on the basis of the reading width of the irradiated area in the direction parallel to the direction of electrophoresis.

(10) The light-receiving subsection is composed of a light-receiving unit of the image sensor of a static induction transistor type, and the direction in which the light is received is nearly parallel to the direction of electrophoresis.

(12) The data from the reading unit may be processed after being transmitted to the data processor unit provided in a location away through a data communication path.

Although the present invention has been specifically described by way of examples, it should be noted that the present invention is understood to be not restricted to the examples and to include variations and modifications within the scope of the invention without departing therefrom.

As have been described hereinabove, the present invention permits an efficient provision of image of distribution of the fluorescent substance without occupying the expensive electrophoresis system of fluorescent type as a whole in analyzing the structure of DNAs by the fluorescence method, for example, by allowing each researcher to use the electrophoresis unit for exclusive purposes and to share the common reading unit with other researchers.

What is claimed is:

1. An electrophoresis pattern reading system of fluorescence-detection type, useful for analyzing a gel-based sample, the sample being labeled with a fluorescent substance that fluoresces upon application of light thereto, comprising:

a detachable migration unit comprising a gel functioning as a base for a sample to be analyzed by electrophoresis and a gel-supporting body for supporting the gel;

an electrophoresis unit, to which the migration unit is detachably mounted, for performing electrophoresis by applying migrating voltage to the gel to which the sample labeled with a fluorescent substance is added; and a reading unit physically separate from the electrophoresis unit for reading an electrophoresis pattern, the reading unit including means for detachably mounting the migration unit detached from and apart from the electrophoresis unit after electrophoresis, and said reading unit having means for passing light to the detachably mounted migration unit and for receiving fluorescence emitted from the fluorescent substance of the sample on the gel upon application of the light.

2. An electrophoresis pattern reading system of fluorescence-detection type as claimed in claim 1, wherein a plurality of electrophoresis units is provided for each reading unit.

3. An electrophoresis pattern reading system of fluorescence-detection type as claimed in claim 1, said means for passing light comprising a spot light source for generating light for exciting fluorescence of the fluorescent substance, a scanning means for scanning light from the spot light source in a direction substantially parallel to the direction of electrophoresis by radiation upon the gel, and a reading section having a light-receiving subsection for receiving fluorescence from the fluorescent substance.

4. An electrophoresis pattern reading system of fluorescence-detection type as claimed in claim 3, wherein the light-receiving subsection comprises a one-dimensional image sensor, wherein the direction in which the light is received is substantially parallel to the direction of electrophoresis.

5. An electrophoresis pattern reading system of fluorescence-detection type as claimed in claim 3, wherein said means for passing light and said scanning means produces the scanning light of a width in the direction perpendicular to the direction of electrophoresis that is extended on the basis of the reading width of the irradiated area in the direction parallel to the direction of electrophoresis.

6. An electrophoresis pattern reading system as claimed in claim 3, wherein the scanning means includes a concave lens for modulating the light from the spot light source.

7. An electrophoresis pattern reading system as claimed in claim 6, wherein the concave lens is arranged to modulate the light from the spot light source to enlarge reading size with respect to a direction substantially perpendicular to the direction of electrophoresis.

8. An electrophoresis pattern reading system as claimed in claim 3, wherein the scanning means includes a convex lens for modulating the light from the spot light source.

9. An electrophoresis pattern reading system as claimed in claim 8, wherein the convex lens is disclosed substantially parallel to the direction of electrophoresis.

10. An electrophoresis pattern reading system as claimed in claim 1, wherein the sample comprises a nucleic acid.

11. An electrophoresis pattern reading system of fluorescence-detection type as claimed in claim 2, said means for passing light comprising a spot light source for generating light for exciting fluorescence of the fluorescent substance, a scanning means for scanning light from the spot light source in a direction substantially parallel to the direction of electrophoresis by radiation upon the gel, and a reading section having a light-receiving subsection for receiving fluorescence from the fluorescent substance.

12. An electrophoresis pattern reading system of fluorescence-detection type as claimed in claim 11, wherein the light-receiving subsection comprises a one-dimensional image sensor, wherein the direction in which the light is received is substantially parallel to the direction of electrophoresis.

13. An electrophoresis pattern reading system of fluorescence-detection type as claimed in claim 11, wherein said means for passing light and said scanning means produces the scanning light of a width in the direction perpendicular to the direction of electrophoresis that is extended on the basis of the reading width of the irradiated area in the direction parallel to the direction of electrophoresis.

14. An electrophoresis pattern reading system as claimed in claim 11, wherein the scanning means includes a concave lens for modulating the light from the spot light source.

15. An electrophoresis pattern reading system as claimed in claim 14, wherein the concave lens is arranged to modulate the light from the spot light source to enlarge reading size with respect to a direction substantially perpendicular to the direction of electrophoresis.

16. An electrophoresis pattern reading system as claimed in claim 11, wherein the scanning means includes a convex lens for modulating the light from the spot light source.

17. An electrophoresis pattern reading system as claimed in claim 16, wherein the convex lens is disclosed substantially parallel to the direction of electrophoresis.

18. An electrophoresis pattern reading system as claimed in claim 2, wherein the sample comprises a nucleic acid.

19. A method for reading an electrophoresis pattern of fluorescence-detection type, comprising:

the step of pouring a sample into a gel in a migration unit, the step of mounting the migration unit in an electrophoresis unit, thereafter the step of performing electrophoresis of the sample, the step of thereafter removing the migration unit with the electrophoresed sample from the electrophoresis unit, the step of mounting the removed migration unit with the electrophoresed sample in a reading unit, and the step of reading the electrophoresis pattern of the electrophoresed sample in the migration unit by the reading unit.

20. A method for reading an electrophoresis pattern of fluorescent type as claimed in claim 19, further comprising the step of providing a plurality of the migration units and a plurality of the electrophoresis units, wherein the step of mounting the migration unit in the reading unit is carried out serially for each of the plurality of the migration units in a common reading unit.

21. A method for reading an electrophoresis pattern of fluorescence-detection type as claimed in claim 19, wherein a direction substantially parallel to a direction of electrophoresis is set as a first direction and a direction perpendicular to the direction of electrophoresis is set as a second direction, and the step of reading the electrophoresis pattern includes the step of defining a pixel size having a longer dimension in the first direction than in the second direction.

22. A method for reading an electrophoresis pattern of fluorescent type as claimed in claim 21, wherein the step of reading the electrophoresis pattern includes the step of obtaining data of a pattern of distribution of the fluorescent substance, and thinning out the data by at least one pixel in the second direction.

23. A method for reading an electrophoresis pattern as claimed in claim 19, wherein said step of pouring uses the sample comprises a nucleic acid.

24. A method for reading an electrophoresis pattern of fluorescence-detection type, comprising:

(a) pouring a plurality of samples one each into a like plurality of gels one each into a like plurality of migration units;
(b) mounting each migration unit one each in a like plurality of electrophoresis units;
(c) thereafter performing electrophoresis of each sample;
(d) thereafter removing one migration unit with its electrophoresed sample from a first one of the plurality of electrophoresis units;
(e) mounting the removed migration unit with its electrophoresed sample in a reading unit;
(f) reading the electrophoresis pattern of the electrophoresis sample in the migration unit by the reading unit; and
(g) repeating the steps (d) through (f) for each remaining electrophoresed sample, and using the same reading unit for each reading step.

* * * * *